(12) United States Patent
Kumar et al.

(10) Patent No.: US 7,829,692 B2
(45) Date of Patent: Nov. 9, 2010

(54) PRIMER COMPOSITION AND A KIT USEFUL FOR THE IDENTIFICATION OF PHYLLANTHUS

(75) Inventors: Shasany Ajit Kumar, Lucknow (IN); Jain Neeraj, Lucknow (IN); Khanuja Suman Preet Singh, Lucknow (IN); Darokar Mahendra Pandurang, Lucknow (IN); Gupta Anil Kumar, Lucknow (IN); Sundaresan Velusamy, Lucknow (IN); Bagchi Guru Das, Lucknow (IN); Singh Subhash Chandra, Lucknow (IN); Singh Janardan, Lucknow (IN); Jain Shital Prasad, Lucknow (IN); Rao Ramachandra Raghavendra, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 243 days.

(21) Appl. No.: 12/058,287

(22) Filed: Mar. 28, 2008

(65) Prior Publication Data

US 2009/0061434 A1    Mar. 5, 2009

Related U.S. Application Data (60) Provisional application No. 60/920,585, filed on Mar. 29, 2007.

(51) Int. Cl.
*C07H 21/04* (2006.01)
*C12P 19/34* (2006.01)

(52) U.S. Cl. .................................. 536/24.33; 435/91.2
(58) Field of Classification Search ...................... None
See application file for complete search history.

(56) References Cited

PUBLICATIONS

International Preliminary Report on Patentability for International Application PCT/IB2007/000802 [online] [retrieved on Jun. 10, 2010] retrieved from http://www.wipo.int/pctdb/images1/PATENTSCOPE/94/a5/98/05a598.pdf.*

Written Opinion of the International Searching Authority for International Application PCT/IB2007/000802 [online] [retrieved on Jun. 10, 2010] retrieved from http://www.wipo.int/pctdb/images1/PATENTSCOPE/94/83/38/058338.pdf.*

International Search Report for International Application PCT/IB2007/000802 [online] [retrieved on Jun. 10, 2010] retrieved from http://www.wipo.int/pctdb/images1/PCT-PAGES/2008/412008/08120027/08120027.pdf.*

Jain et al. SCAR markers for correct identification of Phyllanthus amarus, P. fraternus, P. debilis and P. urinaria used in scientific investigations and dry leaf bulk herb trade. Planta Med 74:296-301 (published online Feb. 26, 2008).*

Dnyaneshwar et al. Development and application of RAPD-SCAR Marker Identification of Phyllanthus emblica LINN. Biol. Pharm. Bull. 29(11):2313-2316, Nov. 2006.*

\* cited by examiner

*Primary Examiner*—Samuel Woolwine
(74) *Attorney, Agent, or Firm*—Seed IP Law Group PLLC (57) ABSTRACT

The present invention relates to an oligonucleotide primer set useful for the identification of *Phyllanthus* at species level, and more particularly, it relates to an oligonucleotide primer set useful for the identification of *Phyllanthus* species selected from the group of 4 specific primer sets and also the invention is directed to a kit useful for the identification of different species of *Phyllanthus* from a mixture.

9 Claims, 2 Drawing Sheets

Figure 1

M: Lambda Hind III marker; 1. *P. amarus,* 2. *P. debilis,* 3. *P. fraternus,* 4. *P. urinaria,* 5. *P.virgatus,* 6. *P.reticulata,* 7. *P.maderaspatensis*

Figure 2

A. *Phyllanthus amarus* specific SCAR marker
Lane 1: DNA Marker λ Hind III digest
Lane 2: DNA fragment generated through *P. amarus* specific SCAR primer pair
Lane 3 to 5: Amplification of *P. fraternus*, *P debilis* and *P. urinaria* with *P. amarus* specific primer pair.

B. *Phyllanthus fraternus* specific SCAR marker
Lane 1: DNA Marker λ Hind III digest
Lane 2: DNA fragment generated through *P. fraternus* specific SCAR primer pair
Lane 3 to 5: Amplification of *P. amarus*, *P debilis* and *P. urinaria* with *P. fraternus* specific primer pair C. *Phyllanthus debilis* specific SCAR marker
Lane 1: DNA Marker λ Hind III + EcoRI digest
Lane 2: DNA fragment generated through *P. debilis* specific SCAR primer pair
Lane 3 to 5: Amplification of *P. amarus*, *P fraternus* and *P. urinaria* with *P. debilis* specific primer pair D. *Phyllanthus urinaria* specific SCAR marker
Lane 1: DNA Marker λ Hind III + EcoRI digest
Lane 2: DNA fragment generated through *P. urinaria* specific SCAR primer pair
Lane 3 to 5: Amplification of *P. amarus*, *P. fraternus* and *P. debilis* with *P. urinaria* specific primer pair.

PRIMER COMPOSITION AND A KIT USEFUL FOR THE IDENTIFICATION OF PHYLLANTHUS

CROSS-REFERENCE TO RELATED APPLICATION

This application claims the benefit under 35 U.S.C. §119 (e) of U.S. Provisional Patent Application No. 60/920,585 filed Mar. 29, 2007; wherein this provisional application is incorporated herein by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 210172_404_SEQUENCE_LISTING.txt. The text file is 10 KB, was created on Mar. 28, 2008, and is being submitted electronically via EFS-Web, concurrent with the filing of the specification.

FIELD OF INVENTION

The present invention relates to an oligonucleotide primer set useful for the identification of *Phyllanthus* at species level.

More particularly, it relates to an oligonucleotide primer set useful for the identification of *Phyllanthus* species selected from the group of 4 specific primer sets.

Further, the invention relates to a kit useful for the identification of different species of *Phyllanthus* from a mixture.

BACKGROUND AND PRIOR ART OF THE INVENTION

The species of *Phyllanthus* have been used since ancient times in different systems of medicine, particularly for the treatment of liver disorders and urinary infections but the concepts and identification of various species, particularly herbaceous ones, have been unclear mainly due to misidentification of specimens in several herbaria. The literature survey and extensive field studies conducted by Chaudhary and Rao (2002), *Phytotaxonomy* 2: 143-162 revealed that out of the 40 species occurring in India, chiefly the allied herbaceous species, like *P. amarus, P. fraternus, P. debilis* are extensively used for jaundice and hepatitis whereas *P. urinaria* for urinary tract infection. These species are also used in stomach ailments like dyspepsia, colic, diarrhea, dysentery, dropsy, urinogenital problems and also as external application for oedomatous swelling and inflammation. These species are important ingredient in many ayurvedic preparations, especially for the treatment of jaundice. This species *Phyllanthus amarus* is distributed throughout India and is considered to be the most widely occurring species of *Phyllanthus* in India.

In recent years, the interest in the plants of the genus *Phyllanthus* has increased considerably due to its therapeutic potential for the treatment of different diseases. Substantial literature on the chemistry and the pharmacological and clinical properties of the genus is available. Different classes of compounds have been isolated from the plants of this genus. Most of these compounds were found to interact with key enzymes of the animal/human system. But most of the time the species are confused or not properly identified leading to adulteration of crude drugs. The genus *Phyllanthus niruri* is non-existent in India. Hence the research works in the name of *P. niruri* is either similar species like *Phyllanthus amarus, Phyllanthus fraternus* or *Phyllanthus debilis*; or abundantly available species of *Phyllanthus urinaria*. So it is necessary to develop a marker system by which the individual species can be differentiated and more specifically the presence of *P. amarus* in the crude drug can be ascertained. Hence systematic experimentation was undertaken to develop a marker system for *P. amarus, P. fraternus, P. debilis* and *P. urinaria*.

Many genetic-marker technologies are adaptable to fingerprinting, including restriction-fragment-length polymorphism (RFLP) Bostein et al. (1980) Am J Hum Genet 32:314-331; single strand conformation polymorphism (SSCP) Fischer et al. (1983) Proc Natl Acad Sci USA 80:1579-1583, Orita et al. (1989) Genomics 5:874-879; amplified fragment-length polymorphism (AFLP) Vos et al. (1995) Nucleic Acids Res 23:4407-4414; microsatellite or single-sequence repeat (SSR) Weber J L and May P E (1989) Am J Hum Genet 44:388-396; rapid-amplified polymorphic DNA (RAPD) Williams et al. (1990) Nucleic Acids Res 18:6531-6535; sequence tagged site (STS) Olson et al. (1989) Science 245:1434-1435; genetic-bit analysis (GBA) Nikiforov et al. (1994) Nucleic Acids Res 22:4167-4175; allele-specific polymerase chain reaction (ASPCR) Gibbs et al. (1989) Nucleic Acids Res 17:2437-2448, Newton et al. (1989) Nucleic Acids Res 17:2503-2516; nick-translation PCR (e.g., TaqMan™) Lee et al. (1993) Nucleic Acids Res 21:3761-3766 and allele-specific hybridization (ASH) Wallace et al. (1979) Nucleic Acids Res 6:3543-3557, (Sheldon et al. (1993) Clinical Chemistry 39(4):718-719) among others. Kits for RAPD and AFLP analyses are commercially available, e.g., from Perkin Elmer Applied Biosystems (Foster City, Calif.). For example, the restriction fragment length polymorphism (RFLP) technique employs restriction enzyme digestion of DNA, followed by size separation of the digested DNA by gel electrophoresis, and hybridization of the size-separated DNA with a specific polynucleotide fragment. Differences in the size of the restriction fragments to which the polynucleotide probe binds reflect sequence differences in DNA samples, or DNA polymorphisms. See Tanksley, Biotechnology 7:257-264 (1988). (McCasky Feazel, et al. 2000. U.S. Pat. No. 6,100,030); (Jain, N et al., Current Science. 85 (10):1454-1458 (2003), (Hosokawa K et al Planta Med. 66(3): 270-2 (2000)).

The novelty of the present invention is the unique DNA sequences those identified by using the simple Randomly amplified polymorphic DNA profile analysis and the methodology by which the SCAR markers can be used to detect or confirm the presence of different species in a crude drug mixture as it is not possible to identify the species in a crude drug morphologically. Also chemical analysis may not be reliable as a species may not produce all the chemicals at all developmental stages. Further the genotypes of plants within the species differ leading to differences in the chemical profiles. Till date full proof commercial methods to identify the species in the mixture of crude drug are not available. It is difficult to identify the investigated species in the intact plants itself and nearly impossible to identify the species in crude drug through conventional methods. So the present invention will help in determining the quality of crude drug with confirmation through these assigned DNA markers.

Mainly the herbaceous species like *P. amarus* Schum. and Thonn, *P. fraternus* Webster and *P. debilis* Klein ex Willd have been reported to be extensively used for jaundice and *P. urinaria* L for urinary tract diseases. Modern research with *Phyllanthus* focuses on its potential for fighting viruses, specifically the hepatitis B virus (Shin et al. *Antiviral Research,*

Figure 1:
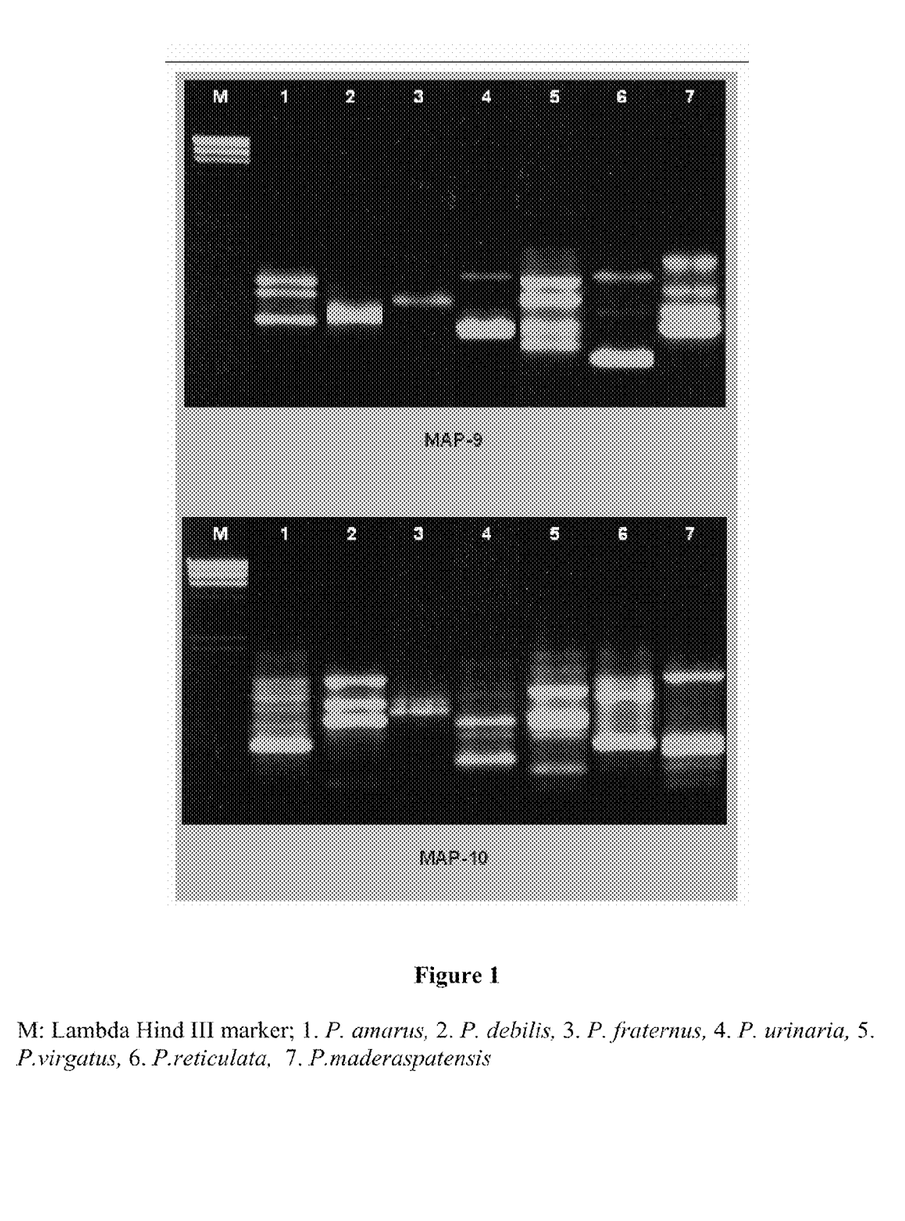
FIG. 1 represents DNA profiles of *Phyllanthus* species generated through amplification with MAP 09 and MAP 10 primers

67,163-168 (2005)) and malaria parasite (Hout et al. *Journal of Ethnopharmacology*, 107, 12-18 (2006)). Despite extensive use for a long time, confusion still prevails over the correct identity and nomenclature of the species as it commonly known as "Bhuianavala" or "Bhumyamalaki" in Indian literature and Ayurveda, representing a group of species comprising of *P. amarus, P. fraternus, P. debilis* and even *P. urinaria* (FIG. 1). Several earlier workers included all these species especially *P. amarus, P. fraternus* and *P. debilis* under a single species *P. niruri* which was later described as '*niruri* complex'. The species *P. niruri* is an American species and not at all found in India. Webster (*Journal of the Arnold Arboretum*, 38,295-373 (1957)) and Mitra and Jain (*Bulletin of the Botanical Survey of India*, 27, 161-176 (1985)) showed that the *P. niruri* of Hooker is actually represented by above described three different species. Thus, confusion in identification of these herbaceous species is largely due to common vernacular names for all the species, similarity in gross morphology, close proximity in the growth habitat and extent of diverse morphological features of the species. This misidentification leads to deliberate or ignorant adulteration of crude drugs, lowering the efficiency of the medication for which it has to be used specifically, leading to decreased or deleterious effect of the drug when administered. So the present study was targeted to develop molecular markers, which would help in unambiguous identification of the above species. The marker can also be used in quality check in dry herbs samples exported from India.

OBJECTS OF THE INVENTION

The main object of the invention is to provide an oligonucleotide primer set useful for the identification of *Phyllanthus* species selected from the group of 4 specific primer sets, comprising the following sequences:

(a) Set 1: (SEQ ID 10 & 11)
    forward primer:
    5'-AGAATTCCGTATCTTCGTATACGTCATGA-3';

reverse primer
    5'-AGAATTCCGTTCAAGCACAGCGGAAGAAG-3';

(b) Set 2: (SEQ ID 12 & 13)
    forward primer
    5'-AGAATTCCGTGTTCTCGTTGAGCAAGGAT-3';

reverse primer
    5'-TGAATTCCGATAGCCCAAAACGCAAAACA-3';

(c) Set 3: (SEQ ID 14 & 15)
    forward primer:
    5'-TGGATCCGCATAGAAATTCAGGAACTAGG-3';

reverse primer:
    5'-TGGATCCGCGGACAACCAATGAGGGACGG-5';

(d) Set 4: (SEQ ID 16 & 17)
    forward primer:
    5'-TGGATCCGCAAAGTGAGAAAATACATATC-3';

reverse primer:
    5'-TGGATCCGCTAGCAAGAAATTATAGCACA-3'.

Further another object of the present invention is to provide a kit useful for the identification of *Phyllanthus* using the primer sets in equal proportions.

Yet another object of the present invention is to provide a kit that is capable to identify the *Phyllanthus* selected from the group comprising *P. amarus, P. fraternus, P. debilis, P. urinaria*.

SUMMARY OF THE INVENTION

The present invention deals with an oligonucleotide primer set for the identification of different species of *Phyllanthus* selected from the group consisting of *Phyllanthus amarus, Phyllanthus fraternus, Phyllanthus debilis, Phyllanthus urinaria* through polymerized chain reaction based detection.

The present invention also provides a kit for identifying the particular species from the mixture of different *Phyllanthus* species.

Accordingly, the present invention provides an oligonucleotide primer set useful for the identification of *Phyllanthus* species selected from the group of following primer sets, comprising the following sequences:

(a) Set 1: (SEQ ID 10 & 11)
    forward primer:
    5'-AGAATTCCGTATCTTCGTATACGTCATGA-3';

reverse primer
    5'-AGAATTCCGTTCAAGCACAGCGGAAGAAG-3';

(b) Set 2: (SEQ ID 12 & 13)
    forward primer
    5'-AGAATTCCGTGTTCTCGTTGAGCAAGGAT-3';

reverse primer
    5'-TGAATTCCGATAGCCCAAAACGCAAAACA-3';

(c) Set 3: (SEQ ID 14 & 15)
    forward primer:
    5'-TGGATCCGCATAGAAATTCAGGAACTAGG-3';

reverse primer:
    5'-TGGATCCGCGGACAACCAATGAGGGACGG-5';

(d) Set 4: (SEQ ID 16 & 17)
    forward primer:
    5'-TGGATCCGCAAAGTGAGAAAATACATATC-3';

reverse primer:
    5'-TGGATCCGCTAGCAAGAAATTATAGCACA-3'.

In an embodiment of the present invention, the primers are used in equal proportions.

In another embodiment of the present invention, the primer Set 1 is useful for identification of *Phyllanthus amarus*.

In yet an embodiment of the present invention, the said primer set of SEQ ID No. 10 and SEQ ID No. 11 is capable to differentiate and identify the presence of *Phyllanthus amarus* by generating a fragment of 1150 base pair when amplified 40 cycles of 1 minute at 94° C., 1 minute at 65° C. and 2 minutes at 72° C. for denaturing, annealing, and extension respectively, with an initial denaturation for 5 minutes at 94° C. and a final extension for 5 minutes at 72° C. after 40 cycles.

In still an embodiment of the present invention, the primer Set 2 is useful for identification of *Phyllanthus fraternus*.

In still an embodiment of the present invention, the said primer set of SEQ ID No. 12 and SEQ ID No. 13 is capable to differentiate and identify the presence of *Phyllanthus fraternus* by generating a fragment of 317 base pair when amplified 40 cycles of 1 minute at 94° C., 1 minute at 55° C. and 1 minutes at 72° C. for denaturing, annealing, and extension respectively, with an initial denaturation for 5 minutes at 94° C. and a final extension for 5 minutes at 72° C. after 40 cycles.

In still another embodiment of the present invention, the primer Set 3 is useful for identification of *Phyllanthus debilis*.

In still an embodiment of the present invention, the said primer set of SEQ ID No. 14 and SEQ ID No. 15 is capable to differentiate and identify the presence of *Phyllanthus debilis* by generating a fragment of 980 base pair when amplified 40 cycles of 1 minute at 94° C., 1 minute at 55° C. and 1.5 minutes at 72° C. for denaturing, annealing, and extension respectively, with an initial denaturation for 5 minutes at 94° C. and a final extension for 5 minutes at 72° C. after 40 cycles.

In yet an embodiment of the present invention, the primer Set 4 is useful for identification of *Phyllanthus urinaria*.

In still an embodiment of the present invention, the said primer set of SEQ ID No. 16 and SEQ ID No. 17 is capable to differentiate and identify the presence of *Phyllanthus urinaria* by generating a fragment of 550 base pair when amplified 40 cycles of 1 minute at 94° C., 1 minute at 55° C. and 1.0 minutes at 72° C. for denaturing, annealing, and extension respectively, with an initial denaturation for 5 minutes at 94° C. and a final extension for 5 minutes at 72° C. after 40 cycles In an embodiment of the present invention, a kit useful for the identification of *Phyllanthus* species, comprises:
  i. sets of oligonucleotide primers as claimed in claim 1;
  ii. reagents and buffers to perform PCR amplification;
  iii. instruction manual to carry out the identification of *Phyllanthus*.

In an embodiment of the present invention, the primers used in the kit are in equal proportion.

In an embodiment of the present invention, the specific *Phyllanthus* species to be identified by the kit is selected from the group comprising *P. amarus, P. fraternus, P. debilis* and *P. urinaria*.

BRIEF DESCRIPTION OF THE INVENTION

DETAILED DESCRIPTION OF THE INVENTION

The present invention is based on the development of a DNA markers based probing kit useful for distinguishing and identification of different species of *Phyllanthus* (*Phyllanthus amarus, Phyllanthus fraternus, Phyllanthus debilis, Phyllanthus urinaria*) used in crude plant based drug through polymerized chain reaction based detection. Further this is related to the identification of specific DNA sequences unique to the species based on which sequence characterized amplified region (SCAR) primer pairs were generated. This provides a method for the detection of species mixture in the crude drug by identifying the specific DNA fragment size present in the amplified product of DNA samples of crude drug using SCAR primer pair.

The following examples are given by way of illustration of the present invention and should not be construed to limit the scope of present invention.

EXAMPLE 1

Collection and Identification of Plant Material

The plant material chosen for analysis consisted of *P. amarus* and its closely related species (*P. fraternus, P. debilis, P. urinaria*), along with some other species like *P. virgatus, P. reticulata, P. maderaspatensis* belonging to the same genus. 93 plants of these species were collected from different parts of the country and randomly 10 plants from each species were taken for further analysis for marker development. These plants were maintained in the glasshouse (CIMAP, Lucknow).

EXAMPLE 2

Isolation of DNA

Total DNA was extracted from approximately 3 g of leaf tissue, from each accession by following the protocol provided by Khanuja et al. (1999). *Plt Mol Biol Repr* 17: 74. The concentration and purity of isolated DNA sample was estimated by taking absorbance at 260 and 280 nm which was also rechecked by loading 2 μl of each sample, in 0.8% agarose gel, along with standard λ DNA.

EXAMPLE 3

RAPD (Randomly Amplified Polymorphic DNA)

The RAPD analysis was carried out for all the accessions using 20 primers (MAP kit) (Khanuja et al., 2000. *Euphytica*. 111: 121-125) and the polymorphism was scored (FIG. 1). The plant material of each of the species was collected from different geographical locations, throughout the country. Twenty plants were collected for each of the accessions. Out of this collection 10 accessions were randomly selected for each of the species to assess the similarity and differences in the profiles. The fragments monomorphic within the species (between the accessions i.e similar fragments present in all the accessions of the same species) but polymorphic between the species were chosen for cloning. For RAPD analysis, polymerase chain reaction was set up for each of the accessions. Amplifications were carried out in 25 μl volume containing 0.6U of Taq DNA polymerase enzyme, 1×Taq Polymerase assay buffer, 10 mM of each of the four dNTPs (dATPs, dCTPs, dGTPs, dTTPs), 5 pmole of random primer and 25 ng of DNA. Amplification was performed in a DNA Engine Thermal Cycler (MJ Research, USA) programmed to 45 cycles of 1 minute at 94° C., 1 minute at 35° C. and 2 minutes at 72° C. for denaturing, annealing, and extension respectively, with an initial denaturation for 5 minutes at 94° C. and a final extension for 5 minutes at 72° C. after 45 cycles (Khanuja et al., 2000. *Euphytica*. 111: 121-125). The amplification products were resolved by electrophoresis on 1.2% agarose gel containing 0.5 μg/ml of ethidium bromide and photographed with Image master VDS (Pharmacia). The bands were analyzed using Image master 1D elite software. Custom-made decanucleotide primers were synthesised in the GRB (Genetic Resources and Biotechnology) Division of CIMAP (Central Institute of Medicinal and Aromatic Plants) on Applied Biosystems 392 DNA-RNA Synthesizer and were designated as MAP01 to MAP20. The sequences of the primers MAP 01 to MAP 20 were AAATCGGAGC (SEQ ID NO:18), GTCCTACTCG (SEQ ID NO:19), GTCCTTAGCG (SEQ ID NO:20), TGCGCGATCG (SEQ ID NO:21), AACGTACGCG (SEQ ID NO:22), GCACGCCGGA (SEQ ID NO:23), CACCCTGCGC (SEQ ID NO:24), CTATCGCCGC (SEQ ID NO:25), CGGGATCCGC (SEQ ID NO:1), GCGAATTCCG (SEQ ID NO:2), CCCTGCAGGC (SEQ ID NO:26), CCAAGCTTGC (SEQ ID NO:27), GTGCAATGAG (SEQ ID NO:28), AGGATACGTG (SEQ ID NO:29), AAGATAGCGG (SEQ ID NO:30), GGATCTGAAC (SEQ ID NO:31), TTGTCTCAGG (SEQ ID NO:32), CATCCCGAAC (SEQ ID NO:33), GGACTCCACG (SEQ ID NO:34), AGCCTGACGC (SEQ ID NO:36), respectively.

All the RAPD profiles thus generated were analyzed for unique band appearing in *P. amarus, P. fraternus, P. debilis* and *P. urinaria* species and absent in the other closely related species. Primer MAP 09 and MAP 10 were finally selected finally as unique species-specific fragments were identified in the RAPD profiles using these primers. The species DNA, primer and the specific unique band size identified have been presented below.

| Species | Size of unique fragment (bp) | RAPD primer that generated the fragment | Sequence of the primer |
|---------|---|---|---|
| P.amarus | 1150 | MAP 10 | GCGAATTCCG (SEQ ID NO: 2) |
| P.fraternus | 317 | MAP 10 | GCGAATTCCG (SEQ ID NO: 2) |
| P.debilis | 980 | MAP 09 | CGGGATCCGC (SEQ ID NO: 1) |
| P.urinaria | 550 | MAP 09 | CGGGATCCGC (SEQ ID NO: 1) |

These bands were also seen to be present for all the accessions of respective species (collected from various locations) in the profile generated through primer MAP 09 and 10 that assured of the consistency of the presence of band in these species and their specificity as the marker for the aforesaid species. The species specific fragments obtained through amplification were cloned in commercially available pBluescript II SK (+) vector.

EXAMPLE 4

Isolation, Cloning and Sequencing Analysis of Species Specific Fragments

The genomic DNA of *Phyllanthus amarus* and *Phyllanthus fraternus* were amplified using specific primer MAP 10 (GCGAATTCCG; Seq Id No. 2) carrying restriction enzyme site EcoR1 (GAATTC). Similar reactions were carried out for *Phyllanthus debilis* and *Phyllanthus urinaria* using primer MAP 09 (CGGGATCCGC; SEQ ID NO: 1) carrying restriction enzyme site BamH1 (GGATCC). The amplification reaction products were run on low melting agarose gel and the specific species identifying fragments as described in example 3 were isolated and purified. These species-specific fragments were cloned in commercially available plasmid pBluescript II SK (+) and transformed into *Escherichia coli* cell (DH5□) strains (Stratagene Inc, USA). The fragments were sequenced using ABI 377 DNA sequencer (Applied Biosystems, USA) from both sides with the help of T7 (Forward) and T3 (Reverse) primers (Stratagene Inc, USA). The following nucleotide sequences were obtained for different species-specific fragments.

*Phyllanthus amarus*

Sequence of the *P. amarus* specific fragment [GRB/EA$_{1150}$F] (SEQ ID NO:3)

5'AGAATTCCGTATCTTCGTATACGTCATGATAGTTAGATCATGTGAAAT
TCATGATAAGCAAATACTATAGACGGATAACCTAGTATTTAAGTTCTGTT
GTATACCAGAGGCAGTCCTGTAAAAGGCTATGTGTGGACTAAAAGAAGGT
GTTATGTCCATTGAAGACTGAAACTTCTGTGTGATGTAATTAAACTGCGC
TCAGTGGATGAGAATACATCACAGCACTATTAAGTATGGTGTGTAATAAG
TTGCCCTGGGCATAGAAAATATTTAAAGATTTTGCCCCCTTTTTCTACTA
GTGGGACACTCGGTACTCATCAAGAGGATCTCTACAGCCCCATTATACCT
GAGAAAATTATTAGACAAGCATACTATTCTCGCCATTTGATTTGTTTTGT
TGAAAAAAATCCGCTACACTTGGTTTTG 3'

Complementary strand of *P. amarus* specific fragment [GRB/EA$_{1150}$ R] (SEQ ID NO:4)

5'AGAATTCCGTTCAAGCACAGCGGAAGAAGATTATAAATAATAACCTAT
CTATCGAAAATCACCCGGATCCACACACGCCTTAGTGTCGATACGGAGTT
GATTCGCCCTCGTTATTACGCGAATATGACGTTTCTAGAAATACTTTTTG
GGAGAGAAATTTCAGATTTCTCTAATCTGAAAAATGTGGGATTTTATGTG
TAAAATCTAAAGTGAATGAAACTTGATCTCATTCTTCTATTCTAGAGAAA
ATAGTGACCTTTCCGAAAAGGTACCTTTTCACTATAATTGCATTTTAGTC
CTGAACTTAATATAGTTTATTTGACGTACTAAACGTCATGGGCGGATAAA
TAATTCTTTCATCTCCCACTCGCACATGACGGTGCGAATCAAACAAACC
TTTTTCTTTGAAACAACCAT 3'

*Phyllanthus fraternus*

Complete sequence of the *P. fraternus* specific fragment [GRB/EF$_{317}$] (SEQ ID NO:5)

5'AGAATTCCGTGTTCTCGTTGAGCAAGGATTTGATTTCTGCGCATTTCG
GTGTCAATCGTTCATTTATTGCTGAGAATTAGGATATTTGCGATTTTGCA
TTTCACGACACTGGTTTTCTTTTTTCGTGCATTTTCCTCGAGAAGAGTTG
TGTTATTTCTCAGTTTTGCACCTAGTATTTCAATTCCTTCTGATTTTGCC
GTTTCGGGTTACAGTGTTCTTGGTTTTTGTTTTATTTTGTTGGTCGAAAT
TGGTTTTGTGCGTAGCCTGGAGCTGAGTATTTGGGTTTCTTG**TGTTTTGC
GTTTTGGGCTATCGGAATTCA**3'

*Phyllanthus debilis*

Sequence of the *P. debilis* specific fragment [GRB/BD$_{980}$F] (SEQ ID NO:6)

5'TGGATCCGCATAGAAATTCAGGAACTAGGATCCTAATTGACCCGAAAA
AATCGAAATTCACAATTACTTAACTTAAATCCCTATGATCTATGATTAGA
TTAGGTATCATTTGAGCAGGCTTGGCAAAACCCTTGTATAGCTTCTTCGA
TTTCTCGATAAAAATAAATCTGACCAACAGTAGTTCGAATGTATATACAA
AGAATTTCTTTTTTTACACTTCTTATTATTAGATAGTGTCCATAAATTTC
ATGATAGGTACCCAAAGGCTCATAATGA3'

Complementary strand of the *P. debilis* specific fragment [BD$_{980}$R] (SEQ ID NO:7)

5'TGGATCCGCGGACAACCAATGAGGGACGGTCATAATAAGGTTTACAAG
TCATTTTCAGATGTAATTGAAGGAAAAGAAGGAAGAATTCGCGAGACTAT
GCTTGGCAAACGAGTTTATTATTCAGGACGTTCTGTCATTGTCGTGTGCC
CCTCACTTTCAATACATCGATGTGGATGCCTCGCGAAATCGCAATAGAGC
TTTTTCAGACATTTGTAATTCGTTGTCTAATTAGACAACATCTTGCTT
3'

*Phyllanthus urinaria*

Sequence of the *P. urinaria* specific fragment [GRB/BU$_{550}$F] (SEQ ID NO:8)

5'TGGATCCGCAAAGTGAGAAAATACATATCAATCGGTGTATTAATACCA
AGGCAAAAGATAGACCACATCTTGGTATAGAAGACCGATAACTAATAACA
GTTGAACACGAAAAAACCGGGAGCGAGGGGTAATTGACCCGACCAACCTA
AGAGATGTGAATGAGAGAAAAGCCTGGTCGGGCCTTTGAATATATTAATT
GGAGTCTGAGGAGAAAGGAATGGCGAGAATAATAATTGACGACAGACAAT
TCATTTATTGCCAAGC3'

Complementary strand of the *P. urinaria* specific fragment [GRB/BU$_{550}$R] (SEQ ID NO:9)

5'TGGATCCGCTAGCAAGAAATTATAGCACACCACACTATTTGAAATGTC
TATGACAAATCAGTGACCTTTACAATTTTACATAATTCTTTTATCCTTTA
ATACCTAGAATTAATATAAGGGCATGGGATCAATCATCCTTATACCATTA
AATCCTTTCTTGGATTCTTCAATGGAATTGGTCAATTCAAAAAAATAATT
TAACTTAATTAATTACCCTGGGGGGCGCCACCTTTCATAGGTCAATGGA
CAAGGGGCCATGGGG3'

EXAMPLE 5

Construction of Sequence Characterized Amplified Region (SCAR) Marker for *Phyllanthus* Species (*P. Amarus, P. Fraternus, P. Debilis* and *P. Urinaria*)

The sequence from both the ends, which included the restriction enzyme site, was taken for synthesizing specific primer to serve as SCAR marker. One base was added before the restriction enzyme site, at the 5' end. The primers finally designed are being presented in below. One forward and one reverse primer were designed from both the ends, respectively and synthesized on Perkin Elmer DNA/RNA Synthesizer ABI 392 (Applied Biosystems, USA). Hence fourth, the primer pairs (Forward and Reverse) are referred as SCAR primers and the species-specific fragment generated by them as SCAR fragment or marker.

Details of Species Specific Primer Pair Synthesized to Generate Scar Markers

| S. No | Species | Primer sequences | Tm (° C.) | % GC conent |
|---|---|---|---|---|
| 1 | P.amarus | Forward primer: 5'AGAATTCCGTATCTTCGTATACGTCATGA 3' (SEQ ID NO: 10) | 55.8 | 34.5 |
| | | Reverse primer: 5'AGAATTCCGTTCAAGCACAGCGGAAGAAG3' (SEQ ID NO: 11) | 61.4 | 48.3 |
| 2 | P.fraternus | Forward primer: 5'AGAATTCCGTGTTCTCGTTGAGCAAGGAT 3' (SEQ ID NO: 12) | 60 | 44.8 |
| | | Reverse primer: 5' TGAATTCCGATAGCCCAAAACGCAAAACA3' (SEQ ID NO: 13) | 58.6 | 41.4 |
| 3 | P.debilis | Forward primer 5'TGGATCCGCATAGAAATTCAGGAACTAGG 3' (SEQ ID NO: 14) | 60 | 44.8 |
| | | Reverse primer 5'TGGATCCGCGGACAACCAATGAGGGACGG 3' (SEQ ID NO: 15) | 67.1 | 62.1 |
| 4 | P.urinaria | Forward primer 5'TGGATCCGCAAAGTGAGAAAATACATATC 3' (SEQ ID NO: 16) | 57.2 | 37.9 |
| | | Reverse primer 5'TGGATCCGCTAGCAAGAAATTATAGCACA 3' (SEQ ID NO: 17) | 58.6 | 41.4 |

Figure 2:
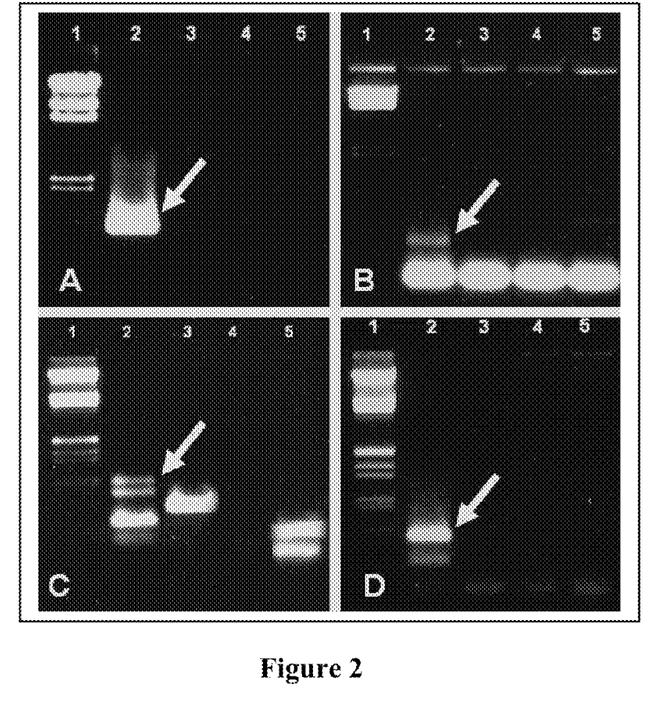
FIG. 2 represents Species specific SCAR markers in *Phyllanthus*.

These primer pairs were used to amplify the DNA of respective species, so as to optimize the conditions for amplification. After optimization of the amplification conditions, SCAR primer pair was used to amplify other closely related species of the same genus along with species for which the specific primer is designed, to ensure that the SCAR primer pair correctly identified the species. PCR products were run on 1.2% agarose gel stained with ethidium bromide (FIG. 2).

Optimized Conditions for Amplification of Scar Markers with Primer Pairs Designed for *Phyllanthus* sps

| Name of the Species | Step I Initial | | Step II | | | | | | | Step III | |
|---|---|---|---|---|---|---|---|---|---|---|---|
| | Denaturation | | Denaturation | | Annealing | | Extension | | | Final extension | |
| | Temp (° C.) | Time (min) | Temp (° C.) | Time (min) | Temp (° C.) | Time (min) | Temp (° C.) | Time (min) | No. of cycles | Temp (° C.) | Time (min) |
| *P. amarus* | 94 | 5 | 94 | 1 | 65 | 1 | 72 | 2 | 40 | 72 | 5 |
| *P. fraternus* | 94 | 5 | 94 | 1 | 55 | 1 | 72 | 1 | 40 | 72 | 5 |
| *P. debilis* | 94 | 5 | 94 | 1 | 60 | 1 | 72 | 1.5 | 40 | 72 | 5 |
| *P. urinaria* | 94 | 5 | 94 | 1 | 55 | 1 | 72 | 1 | 40 | 72 | 5 |

The species-specific primer pairs generated different amplification products for each of the respective species when amplified using the optimized conditions. *P. amarus* specific primer pair generated a single fragment of 1150 bp with DNA sample of *P. amarus* and no product with other species amplified simultaneously, as control. The *P. fraternus* specific primer pair produced fragment of about 317 bp with the DNA sample of *P. fraternus* and a fragment of low intensity of about 500 bp with DNA sample of *P. urinaria* and no fragments with the DNA samples of other species. The primer pair specific to *P. debilis* generated a fragment of 980 bp with DNA sample of *P. debilis*. *P. debilis* DNA also produced two lighter fragments of 564 bp and 125 bp. This primer pair also generated a fragment of 125 bp in other species i.e. *P. urinaria* and *P. reticulata* in addition to *P. debilis* whereas a heavy fragment (about 500 bp) was obtained with *P. amarus* DNA. The primer pair specific to *P. urinaria* amplified two fragments of about 550 bp and 200 bp with the DNA sample of *P. urinaria* and no fragments with the DNA sample of other species amplified with the same primer pair. These SCAR primers identified the presence of species in a crude drug mixture. The methodology for identification is provided in the next example.

EXAMPLE 6

Methodology for Identification of Different Species of *Phyllanthus*

DNA Isolation

DNA Sample was isolated from crude drug mixture following the protocol of Khanuja et al., (1999). *Plt Mol Bio Repor.* 17: 74.

Detection of *Phyllanthus amarus* in the Crude Drug Mixture Using SCAR Primer Pair
  1. Amplification of DNA using
    a. Forward primer:

5'AGAATTCCGTATCTTCGTATACGTCATGA 3' (SEQ ID NO: 10)

Reverse primer:

5'AGAATTCCGTTCAAGCACAGCGGAAGAAG3' (SEQ ID NO: 11)

b. Following the protocol of Khanuja et al., 2000. *Euphytica.* 111: 121-125.
  c. In a thermal cycler programmed to 40 cycles of 1 minute at 94° C., 1 minute at 65° C. and 2 minutes at 72° C. for denaturing, annealing, and extension respectively, with an initial denaturation for 5 minutes at 94° C. and a final extension for 5 minutes at 72° C. after 40 cycles.
  d. The amplification products were resolved by electrophoresis on 1.2% agarose gel containing 0.5 μg/ml of ethidium bromide and photographed with Image master VDS (Pharmacia). The bands were analyzed using Image master 1D elite software.
  2. *P. amarus* specific primer pair generates a single fragment of 1150 bp with DNA sample of *P. amarus* and not with other species amplified simultaneously, as control. This identifies the presence of *P. amarus* in crude drug mixture.

Detection of *Phyllanthus fraternus* in the Crude Drug Mixture Using SCAR Primer Pair
  1. Amplification of DNA using
    a. Forward primer:

5'AGAATTCCGTGTTCTCGTTGAGCAAGGAT 3' (SEQ ID NO: 12)

Reverse primer: 5'

TGAATTCCGATAGCCCAAAACGCAAAACA3' (SEQ ID NO: 13)

b. Following the protocol of Khanuja et al., 2000. *Euphytica.* 111: 121-125
  c. In a thermal cycler programmed to 40 cycles of 1 minute at 94° C., 1 minute at 55° C. and 1 minutes at 72° C. for denaturing, annealing, and extension respectively, with an initial denaturation for 5 minutes at 94° C. and a final extension for 5 minutes at 72° C. after 40 cycles.
  d. The amplification products were resolved by electrophoresis on 1.2% agarose gel containing 0.5 μg/ml of ethidium bromide and photographed with Image master VDS (Pharmacia). The bands were analyzed using Image master 1D elite software.

2. *P. fraternus* specific primer pair produces fragment of about 317 bp with the DNA sample of *P. fraternus* and a fragment of low intensity of about 500 bp with DNA sample of *P. urinaria* and no fragments with the DNA samples of other species. This SCAR marker of 312 bp generated from specific SCAR primers identifies *P. fraternus* in crude drug mixture.

Detection of *Phyllanthus debilis* in the Crude Drug Mixture Using SCAR Primer Pair 1. Amplification of DNA using
   a. Forward primer: 5'

TGGATCCGCATAGAAATTCAGGAACTAGG 3' (SEQ ID NO: 14)

Reverse primer: 5'

TGGATCCGCGGACAACCAATGAGGGACGG 3' (SEQ ID NO: 15)

b. Following the protocol of Khanuja et al., 2000. *Euphytica*. 111: 121-125
   c. In a thermal cycler programmed to 40 cycles of 1 minute at 94° C., 1 minute at 60° C. and 1.5 minutes at 72° C. for denaturing, annealing, and extension respectively, with an initial denaturation for 5 minutes at 94° C. and a final extension for 5 minutes at 72° C. after 40 cycles.
   d. The amplification products were resolved by electrophoresis on 1.2% agarose gel containing 0.5 µg/ml of ethidium bromide and photographed with Image master VDS (Pharmacia). The bands were analyzed using Image master 1D elite software.

2. The primer pair specific to *P. debilis* generates a fragment of 980 bp with DNA sample of *P. debilis*. *P. debilis* DNA also produced two lighter fragments of 564 bp and 125 bp. This primer pair also generated a fragment of 125 bp in other species i.e. *P. urinaria* and P. *reticulata* in addition to *P. debilis* whereas a heavy fragment (about 500 bp) was obtained with *P. amarus* DNA. So the presence of 980 bp fragment identifies *P. debilis*.

Detection of *Phyllanthus urinaria* in the Crude Drug Mixture Using SCAR Primer Pair 1. Amplification of DNA using
   a. Forward primer:

5'TGGATCCGCAAAGTGAGAAAATACATATC 3' (SEQ ID NO: 16)

Reverse primer:

5'TGGATCCGCTAGCAAGAAATTATAGCACA 3' (SEQ ID NO: 17)

b. Following the protocol of Khanuja et al., 2000. *Euphytica*. 111: 121-125
   c. In a thermal cycler programmed to 40 cycles of 1 minute at 94° C., 1 minute at 55° C. and 1 minutes at 72° C. for denaturing, annealing, and extension respectively, with an initial denaturation for 5 minutes at 94° C. and a final extension for 5 minutes at 72° C. after 40 cycles.
   d. The amplification products were resolved by electrophoresis on 1.2% agarose gel containing 0.5 µg/ml of ethidium bromide and photographed with Image master VDS (Pharmacia). The bands were analyzed using Image master 1D elite software.

2. The primer pair specific to *P. urinaria* amplified two fragments of about 550 bp and 200 bp with the DNA sample of *P. urinaria* and no fragments with the DNA sample of other species amplified with the same primer pair. This SCAR marker identifies *P. urinaria*

ADVANTAGES

The main advantages of the present invention are:
i. The present invention is useful for detecting the presence of species in dry leaf samples exported as bulk herbal drug.
ii. The present invention is useful for identifying correct species for use in research related to activity purpose.

All of the above U.S. patents, U.S. patent application publications, U.S. patent applications, foreign patents, foreign patent applications and non-patent publications referred to in this specification and/or listed in the Application Data Sheet, including but not limited to U.S. No. 60/920,585, are incorporated herein by reference, in their entirety.

We claim:

1. An oligonucleotide primer set for identifying a *Phyllanthus* species, comprising a primer set that comprises a forward primer and a reverse primer and that is selected from the group consisting of:
   (a) an oligonucleotide primer set that comprises a forward oligonucleotide primer having the nucleotide sequence set forth in SEQ ID NO:10 (5'-AGAATTCCGTATCTTCGTATACGTCATGA-3') and a reverse oligonucleotide primer having the nucleotide sequence set forth in SEQ ID NO:11 (5'-AGAATTCCGTTCAAGCACAGCGGAAGAAG-3');
   (b) an oligonucleotide primer set that comprises a forward oligonucleotide primer having the nucleotide sequence set forth in SEQ ID NO:12 (5'-AGAATTCCGTGTTCTCGTTGAGCAAGGAT-3') and a reverse oligonucleotide primer having the nucleotide sequence set forth in SEQ ID NO:13 (5'-TGAATTCCGATAGCCCAAAACGCAAAACA-3');
   (c) an oligonucleotide primer set that comprises a forward oligonucleotide primer having the nucleotide sequence set forth in SEQ ID NO:14 (5'-TGGATCCGCATAGAAATTCAGGAACTAGG-3') and a reverse oligonucleotide primer having the nucleotide sequence set forth in SEQ ID NO:15 (5'-TGGATCCGCGGACAACCAATGAGGGACGG-5'); and
   (d) an oligonucleotide primer set that comprises a forward oligonucleotide primer having the nucleotide sequence set forth in SEQ ID NO:16 (5'-TGGATCCGCAAAGTGAGAAAATACATATC-3') and a reverse oligonucleotide primer having the nucleotide sequence set forth in SEQ ID NO:17 (5'-TGGATCCGCTAGCAAGAAATTATAGCACA-3').

2. The oligonucleotide primer set of claim 1, wherein the forward and reverse primers are present in equal proportions.

3. The oligonucleotide primer set of claim 1 (a), wherein the *Phyllanthus* species is *Phyllanthus amarus*.

4. The oligonucleotide primer set of claim 1 (b), wherein the *Phyllanthus* species is *Phyllanthus fraternus*.

5. The oligonucleotide primer set of claim 1 (c), wherein the *Phyllanthus* species is *Phyllanthus debilis*.

6. The oligonucleotide primer set of claim 1 (d), wherein the *Phyllanthus* species is *Phyllanthus urinaria*.

7. A kit for identifying a *Phyllanthus* species, which comprises:
   (i) an oligonucleotide primer set that comprises a forward primer and a reverse primer and that comprises one or more sets selected from the group consisting of:
      (a) an oligonucleotide primer set that comprises a forward oligonucleotide primer having the nucleotide sequence set forth in SEQ ID NO:10 (5'-AGAATTCCGTATCTTCGTATACGTCATGA-3') and a reverse oligonucleotide primer having the nucleotide sequence set forth in SEQ ID NO:11 (5'-AGAATTCCGTTCAAGCACAGCGGAAGAAG-3');
      (b) an oligonucleotide primer set that comprises a forward oligonucleotide primer having the nucleotide sequence set forth in SEQ ID NO:12 (5'-AGAATTCCGTGTTCTCGTTGAGCAAGGAT-3') and a reverse oligonucleotide primer having the nucleotide sequence set forth in SEQ ID NO:13 (5'-TGAATTCCGATAGCCCAAAACGCAAAACA-3');
      (c) an oligonucleotide primer set that comprises a forward oligonucleotide primer having the nucleotide sequence set forth in SEQ ID NO:14 (5'-TGGATCCGCATAGAAATTCAGGAACTAGG-3') and a reverse oligonucleotide primer having the nucleotide sequence set forth in SEQ ID NO:15 (5'-TGGATCCGCGGACAACCAATGAGGGACGG-5'); and
      (d) an oligonucleotide primer set that comprises a forward oligonucleotide primer having the nucleotide sequence set forth in SEQ ID NO:16 (5'-TGGATCCGCAAAGTGAGAAAATACATATC-3') and a reverse oligonucleotide primer having the nucleotide sequence set forth in SEQ ID NO:17 (5'-TGGATCCGCTAGCAAGAAATTATAGCACA-3');
   (ii) reagents and buffers to perform PCR amplification; and
   (iii) an instruction manual.

8. The kit of claim 7, wherein the forward and reverse primers are present in equal proportion.

9. The kit of claim 7, wherein the *Phyllanthus* species is selected from the group consisting of *P. amarus*, *P. fraternus*, *P. debilis* and *P. urinaria*.

* * * * *

SEQUENCE LISTING

<160> NUMBER OF SEQ ID NOS: 35

<210> SEQ ID NO 1
<211> LENGTH: 10
<212> TYPE: DNA
<213> ORGANISM: Artificial Sequence
<220> FEATURE:
<223> OTHER INFORMATION: Synthesized decanucleotide primer designated
      MAP 09

<400> SEQUENCE: 1
cgggatccgc                                                          10

<210> SEQ ID NO 2
<211> LENGTH: 10
<212> TYPE: DNA
<213> ORGANISM: Artificial Sequence
<220> FEATURE:
<223> OTHER INFORMATION: Synthesized decanucleotide primer designated
      MAP 10

<400> SEQUENCE: 2

| gcgaattccg | 10 |

<210> SEQ ID NO 3
<211> LENGTH: 426
<212> TYPE: DNA
<213> ORGANISM: Phyllanthus amarus

<400> SEQUENCE: 3

| agaattccgt atcttcgtat acgtcatgat agttagatca tgtgaaattc atgataagca | 60 |
| aatactatag acggataacc tagtatttaa gttctgttgt ataccagagg cagtcctgta | 120 |
| aaaggctatg tgtggactaa agaaggtgt tatgtccatt gaagactgaa acttctgtgt | 180 |
| gatgtaatta aactgcgctc agtggatgag aatacatcac agcactatta agtatggtgt | 240 |
| gtaataagtt gccctgggca tagaaaatat ttaaagattt tgccccctttt ttctactagt | 300 |
| gggacactcg gtactcatca agaggatctc tacagcccca ttatacctga aaaattatt | 360 |
| agacaagcat actattctcg ccatttgatt tgttttgttg aaaaaaatcc gctacacttg | 420 |
| gttttg | 426 |

<210> SEQ ID NO 4
<211> LENGTH: 418
<212> TYPE: DNA
<213> ORGANISM: Phyllanthus amarus

<400> SEQUENCE: 4

| agaattccgt tcaagcacag cggaagaaga ttataaataa taacctatct atcgaaaatc | 60 |
| acccggatcc acacacgcct tagtgtcgat acggagttga ttcgccctcg ttattacgcg | 120 |
| aatatgacgt ttctagaaat acttttttggg agagaaattt cagatttctc taatctgaaa | 180 |
| aatgtgggat tttatgtgta aaatctaaag tgaatgaaac ttgatctcat tcttctattc | 240 |
| tagagaaaat agtgaccttt ccgaaaaggt accttttcac tataattgca ttttagtcct | 300 |
| gaacttaata tagtttattt gacgtactaa acgtcatggg cggataaata attctttcat | 360 |
| ctcccactcg cacatgacgg tgcgaatcaa acaaaacctt tttctttgaa acaaccat | 418 |

<210> SEQ ID NO 5
<211> LENGTH: 319
<212> TYPE: DNA
<213> ORGANISM: Phyllanthus fraternus

<400> SEQUENCE: 5

| agaattccgt gttctcgttg agcaaggatt tgatttctgc gcatttcggt gtcaatcgtt | 60 |
| catttattgc tgagaattag gatatttgcg attttgcatt tcacgacact ggttttcttt | 120 |
| tttcgtgcat tttcctcgag aagagttgtg ttatttctca gttttgcacc tagtatttca | 180 |
| attccttctg attttgccgt ttcgggttac agtgttcttg gttttgttt tattttgttg | 240 |
| gtcgaaattg gttttgtgcg tagcctggag ctgagtattt gggtttcttg tgttttgcgt | 300 |
| tttgggctat cggaattca | 319 |

<210> SEQ ID NO 6
<211> LENGTH: 276
<212> TYPE: DNA
<213> ORGANISM: Phyllanthus debilis

<400> SEQUENCE: 6

| tggatccgca tagaaattca ggaactagga tcctaattga cccgaaaaaa tcgaaattca | 60 |

```
caattactta acttaaatcc ctatgatcta tgattagatt aggtatcatt tgagcaggct      120
tggcaaaacc cttgtatagc ttcttcgatt tctcgataaa aataaatctg accaacagta      180
gttcgaatgt atatacaaag aatttctttt tttacacttc ttattattag atagtgtcca      240
taaatttcat gataggtacc caaaggctca taatga                               276

<210> SEQ ID NO 7
<211> LENGTH: 246
<212> TYPE: DNA
<213> ORGANISM: Phyllanthus debilis

<400> SEQUENCE: 7
tggatccgcg gacaaccaat gagggacggt cataataagg tttacaagtc attttcagat       60
gtaattgaag gaaaagaagg aagaattcgc gagactatgc ttggcaaacg agtttattat      120
tcaggacgtt ctgtcattgt cgtgtgcccc tcactttcaa tacatcgatg tggatgcctc      180
gcgaaatcgc aatagagctt tttcagacat ttgtaattcg ttgtctaatt agacaacatc      240
ttgctt                                                                 246

<210> SEQ ID NO 8
<211> LENGTH: 264
<212> TYPE: DNA
<213> ORGANISM: Phyllanthus urinaria

<400> SEQUENCE: 8
tggatccgca aagtgagaaa atacatatca atcggtgtat taataccaag gcaaaagata       60
gaccacatct tggtatagaa gaccgataac taataacagt tgaacacgaa aaaaccggga      120 gcgagggta attgacccga ccaacctaag agatgtgaat gagagaaaag cctggtcggg       180
cctttgaata tattaattgg agtctgagga gaaaggaatg gcgagaataa taattgacga      240
cagacaattc atttattgcc aagc                                             264

<210> SEQ ID NO 9
<211> LENGTH: 264
<212> TYPE: DNA
<213> ORGANISM: Phyllanthus urinaria

<400> SEQUENCE: 9
tggatccgct agcaagaaat tatagcacac cacactattt gaaatgtcta tgacaaatca       60 gtgacccttta caatttttaca taattctttt atcctttaat acctagaatt aatataaggg     120
catgggatca atcatcctta taccattaaa tcctttcttg gattcttcaa tggaattggt      180
caattcaaaa aaataattta acttaattaa ttaccctggg ggggcgccac ctttcatagg      240
tcaatggaca aggggggccat gggg                                            264

<210> SEQ ID NO 10
<211> LENGTH: 29
<212> TYPE: DNA
<213> ORGANISM: Artificial Sequence
<220> FEATURE:
<223> OTHER INFORMATION: Forward primer of SCAR primer pair specific to
      P.amarus

<400> SEQUENCE: 10
agaattccgt atcttcgtat acgtcatga                                         29

<210> SEQ ID NO 11
<211> LENGTH: 28
```

-continued

```
<212> TYPE: DNA
<213> ORGANISM: Artificial Sequence
<220> FEATURE:
<223> OTHER INFORMATION: Reverse primer of SCAR primer pair specific to
      P.amarus

<400> SEQUENCE: 11
agaattccgt tcaagcacag cggaagaa                                         28

<210> SEQ ID NO 12
<211> LENGTH: 29
<212> TYPE: DNA
<213> ORGANISM: Artificial Sequence
<220> FEATURE:
<223> OTHER INFORMATION: Forward primer of SCAR primer pair specific to
      P.fraternus

<400> SEQUENCE: 12
agaattccgt gttctcgttg agcaaggat                                        29

<210> SEQ ID NO 13
<211> LENGTH: 29
<212> TYPE: DNA
<213> ORGANISM: Artificial Sequence
<220> FEATURE:
<223> OTHER INFORMATION: Reverse primer of SCAR primer pair specific to
      P.fraternus

<400> SEQUENCE: 13
tgaattccga tagcccaaaa cgcaaaaca                                        29

<210> SEQ ID NO 14
<211> LENGTH: 29
<212> TYPE: DNA
<213> ORGANISM: Artificial Sequence
<220> FEATURE:
<223> OTHER INFORMATION: Forward primer of SCAR primer pair specific to
      P.debilis

<400> SEQUENCE: 14
tggatccgca tagaaattca ggaactagg                                        29

<210> SEQ ID NO 15
<211> LENGTH: 29
<212> TYPE: DNA
<213> ORGANISM: Artificial Sequence
<220> FEATURE:
<223> OTHER INFORMATION: Reverse primer of SCAR primer pair specific to
      P.debilis

<400> SEQUENCE: 15
tggatccgcg gacaaccaat gagggacgg                                        29

<210> SEQ ID NO 16
<211> LENGTH: 29
<212> TYPE: DNA
<213> ORGANISM: Artificial Sequence
<220> FEATURE:
<223> OTHER INFORMATION: Forward primer of SCAR primer pair specific to
      P.urinaria

<400> SEQUENCE: 16
tggatccgca aagtgagaaa atacatatc                                        29

<210> SEQ ID NO 17
<211> LENGTH: 29
<212> TYPE: DNA
```

```
<213> ORGANISM: Artificial Sequence
<220> FEATURE:
<223> OTHER INFORMATION: Reverse primer of SCAR primer pair specific to
      P.urinaria

<400> SEQUENCE: 17
tggatccgct agcaagaaat tatagcaca                                      29

<210> SEQ ID NO 18
<211> LENGTH: 10
<212> TYPE: DNA
<213> ORGANISM: Artificial Sequence
<220> FEATURE:
<223> OTHER INFORMATION: Synthesized decanucleotide primer designated
      MAP 01

<400> SEQUENCE: 18
aaatcggagc                                                           10

<210> SEQ ID NO 19
<211> LENGTH: 10
<212> TYPE: DNA
<213> ORGANISM: Artificial Sequence
<220> FEATURE:
<223> OTHER INFORMATION: Synthesized decanucleotide primer designated
      MAP 02

<400> SEQUENCE: 19
gtcctactcg                                                           10

<210> SEQ ID NO 20
<211> LENGTH: 10
<212> TYPE: DNA
<213> ORGANISM: Artificial Sequence
<220> FEATURE:
<223> OTHER INFORMATION: Synthesized decanucleotide primer designated
      MAP 03

<400> SEQUENCE: 20
gtccttagcg                                                           10

<210> SEQ ID NO 21
<211> LENGTH: 10
<212> TYPE: DNA
<213> ORGANISM: Artificial Sequence
<220> FEATURE:
<223> OTHER INFORMATION: Synthesized decanucleotide primer designated
      MAP 04

<400> SEQUENCE: 21
tgcgcgatcg                                                           10

<210> SEQ ID NO 22
<211> LENGTH: 10
<212> TYPE: DNA
<213> ORGANISM: Artificial Sequence
<220> FEATURE:
<223> OTHER INFORMATION: Synthesized decanucleotide primer designated
      MAP 05

<400> SEQUENCE: 22
aacgtacgcg                                                           10

<210> SEQ ID NO 23
<211> LENGTH: 10
<212> TYPE: DNA
<213> ORGANISM: Artificial Sequence
```

```
<220> FEATURE:
<223> OTHER INFORMATION: Synthesized decanucleotide primer designated
      MAP 06

<400> SEQUENCE: 23
gcacgccgga                                                            10

<210> SEQ ID NO 24
<211> LENGTH: 10
<212> TYPE: DNA
<213> ORGANISM: Artificial Sequence
<220> FEATURE:
<223> OTHER INFORMATION: Synthesized decanucleotide primer designated
      MAP 07

<400> SEQUENCE: 24
caccctgcgc                                                            10

<210> SEQ ID NO 25
<211> LENGTH: 10
<212> TYPE: DNA
<213> ORGANISM: Artificial Sequence
<220> FEATURE:
<223> OTHER INFORMATION: Synthesized decanucleotide primer designated
      MAP 08

<400> SEQUENCE: 25
ctatcgccgc                                                            10

<210> SEQ ID NO 26
<211> LENGTH: 10
<212> TYPE: DNA
<213> ORGANISM: Artificial Sequence
<220> FEATURE:
<223> OTHER INFORMATION: Synthesized decanucleotide primer designated
      MAP 11

<400> SEQUENCE: 26
ccctgcaggc                                                            10

<210> SEQ ID NO 27
<211> LENGTH: 10
<212> TYPE: DNA
<213> ORGANISM: Artificial Sequence
<220> FEATURE:
<223> OTHER INFORMATION: Synthesized decanucleotide primer designated
      MAP 12

<400> SEQUENCE: 27
ccaagcttgc                                                            10

<210> SEQ ID NO 28
<211> LENGTH: 10
<212> TYPE: DNA
<213> ORGANISM: Artificial Sequence
<220> FEATURE:
<223> OTHER INFORMATION: Synthesized decanucleotide primer designated
      MAP 13

<400> SEQUENCE: 28
gtgcaatgag                                                            10

<210> SEQ ID NO 29
<211> LENGTH: 10
<212> TYPE: DNA
<213> ORGANISM: Artificial Sequence
<220> FEATURE:
```

-continued

<223> OTHER INFORMATION: Synthesized decanucleotide primer designated
      MAP 14

<400> SEQUENCE: 29
aggatacgtg                                                                 10

<210> SEQ ID NO 30
<211> LENGTH: 10
<212> TYPE: DNA
<213> ORGANISM: Artificial Sequence
<220> FEATURE:
<223> OTHER INFORMATION: Synthesized decanucleotide primer designated
      MAP 15

<400> SEQUENCE: 30
aagatagcgg                                                                 10

<210> SEQ ID NO 31
<211> LENGTH: 10
<212> TYPE: DNA
<213> ORGANISM: Artificial Sequence
<220> FEATURE:
<223> OTHER INFORMATION: Synthesized decanucleotide primer designated
      MAP 16

<400> SEQUENCE: 31
ggatctgaac                                                                 10

<210> SEQ ID NO 32
<211> LENGTH: 10
<212> TYPE: DNA
<213> ORGANISM: Artificial Sequence
<220> FEATURE:
<223> OTHER INFORMATION: Synthesized decanucleotide primer designated
      MAP 17

<400> SEQUENCE: 32
ttgtctcagg                                                                 10

<210> SEQ ID NO 33
<211> LENGTH: 10
<212> TYPE: DNA
<213> ORGANISM: Artificial Sequence
<220> FEATURE:
<223> OTHER INFORMATION: Synthesized decanucleotide primer designated
      MAP 18

<400> SEQUENCE: 33
catcccgaac                                                                 10

<210> SEQ ID NO 34
<211> LENGTH: 10
<212> TYPE: DNA
<213> ORGANISM: Artificial Sequence
<220> FEATURE:
<223> OTHER INFORMATION: Synthesized decanucleotide primer designated
      MAP 19

<400> SEQUENCE: 34
ggactccacg                                                                 10

<210> SEQ ID NO 35
<211> LENGTH: 10
<212> TYPE: DNA

-continued

```
<213> ORGANISM: Artificial Sequence
<220> FEATURE:
<223> OTHER INFORMATION: Synthesized decanucleotide primer designated
      MAP 20

<400> SEQUENCE: 35
agcctgacgc                                                            10
```